(12) United States Patent
Vance et al.

(10) Patent No.: US 7,734,482 B1
(45) Date of Patent: Jun. 8, 2010

(54) SYSTEM AND METHOD FOR PRE-ADMISSION TESTING

(76) Inventors: Earl D. Vance, 291 Florence Dr., Pickerington, OH (US) 43147; Joseph A. Mack, 704 Lindsey Marie La., Columbus, OH (US) 43235; Nicholas P. Nelson, 6388 Skipping Stone Dr., New Albany, OH (US) 43054

( * ) Notice: Subject to any disclaimer, the term of this patent is extended or adjusted under 35 U.S.C. 154(b) by 754 days.

(21) Appl. No.: 11/535,792

(22) Filed: Sep. 27, 2006

(51) Int. Cl.
  *A61F 5/00* (2006.01)
  *G06F 19/00* (2006.01)
(52) U.S. Cl. .......................................................... 705/3
(58) Field of Classification Search ..................... 705/2, 705/3
  See application file for complete search history.

(56) References Cited

U.S. PATENT DOCUMENTS

| | | | | |
|---|---|---|---|---|
| 5,970,466 | A * | 10/1999 | Detjen et al. | 705/8 |
| 2002/0131572 | A1* | 9/2002 | Paradis | 379/200 |
| 2004/0146156 | A1* | 7/2004 | Wellons et al. | 379/265.09 |
| 2005/0075906 | A1* | 4/2005 | Kaindl et al. | 705/2 |
| 2005/0275871 | A1* | 12/2005 | Baird et al. | 358/1.15 |

\* cited by examiner

*Primary Examiner*—Gerald J. O'Connor
*Assistant Examiner*—Trang Nguyen
(74) *Attorney, Agent, or Firm*—Standley Law Group LLP

(57) ABSTRACT

A system and method for scheduling pre-admission testing (PAT) appointments and accessing PAT reports through an on-line interface. The system and method allows the input of patient demographic and medical information from a remote location. PAT physicians can access scheduling information and input patient information using an electronic medical record module.

47 Claims, 22 Drawing Sheets

SYSTEM AND METHOD FOR PRE-ADMISSION TESTING

The present invention relates generally to a system and method for checking in and scheduling pre-admission testing patients.

BACKGROUND AND SUMMARY OF THE INVENTION

Pre-Admission Testing (PAT), sometimes referred to as PreOperative Clearance is a common process in use at hospitals and surgery centers across the nation. When a surgeon sees a patient and determines that surgery is needed, the surgeon will schedule a PAT to make sure that the patient is healthy enough for the surgery and to determine any medication or therapy changes the patient needs prior to surgery (i.e. prophylactic antibiotics or stopping blood thinners). Usually, the surgeon is not qualified to do the PAT. PATs are typically done by physicians with Internal Medicine or Family Practice specialties, since they are trained to look at the patient's entire medical history and current therapies with a much broader perspective than a surgeon who might be focusing on the required surgery for the patient.

PATs serve multiple purposes, including:
1) Making sure the patient is medically ready for the surgery and if the results are inconclusive, to order the necessary follow up tests to determine if the patient is medically ready for the surgery.
2) Making sure that the patient has all the required lab work completed for their surgery and past medical history before the day of surgery.
3) Change medical therapy to prepare the patient for surgery (i.e. stop blood thinners, preoperative antibiotics).
4) Prevent same day surgery cancellations by the anesthesiologist or surgeon due to the patient not being medically ready for the surgery.

When a surgeon determines that a patient needs surgery, the surgeon will try to schedule a PAT. This is often done through the patient's primary care physician (PCP) or through the hospital or surgery center where the surgery will be performed. Either option can be very difficult for the surgeon and patient. If the surgeon tries to schedule the surgery through the patient's PCP, they can have a hard time getting the patient scheduled for the PAT before the surgery date. Also, the patient's PCP is rarely aware of all the testing requirements of the hospital or surgery center. If the surgeon is lucky enough to get the PCP to see the patient in time, they are often given a PAT from the PCP that will not be accepted by the surgery center or hospital due to the PCP's unfamiliarity with surgery center or hospital's PAT requirements. Even when the PCP can get the patient scheduled in time and delivers a complete PAT, the burden is on the surgeon's office to make sure that the PCP's PAT report and all necessary lab results are forwarded to the surgery center or hospital.

If the patient's PCP is unable or unwilling to do the PAT, the surgeon can sometimes turn to the hospital's PAT department to have a physician supplied by the hospital complete the patient's PAT (surgery centers typically do not have a high enough volume to make supplying their own PAT clinic feasible). Unfortunately, most hospitals PAT clinics are designed around the hospital's needs and not the surgeon's or patient's. This can result in a cumbersome PAT scheduling process where the surgeon's office calls the PAT clinic only to have to leave a voicemail. When the PAT clinic calls back, the patient is no longer in the surgeon's office and now the surgeon's office is forced to play "phone tag" with the patient and act as an unnecessary middle man to schedule the patient for their PAT. The PAT clinic's report is rarely in an easy to read format for the surgeon and the responsibility for follow up testing is often left to the surgeon instead of the PAT clinic. Finally, if the surgeon operates at multiple hospitals, they have multiple PAT clinics and procedures that they need to deal with.

The present system is designed to streamline the PAT process for the surgeon, patient, and surgical facility. The components of the system preferably support multiple surgical specialties and surgical facilities and are aware of requirements unique to each surgeon and/or surgical facility. The system can be utilized by a PAT clinic to significantly improve the PAT experience for all stakeholders.

When a surgeon decides to utilize a PAT clinic that uses the invention of the present invention, their experience is vastly improved. First, when the surgeon decides to schedule a patient for surgery, they preferably go to an on-line web site such as www.patclinic.com to enter basic demographic information about the patient and their surgery as well as schedule a PAT time. In some cases, the PAT must be done that day (i.e. the patient is from out of town and doesn't want to make a special trip back or the surgery is scheduled within the next few days). If the PAT must be done the same day, the system text pages the PAT physician and ancillary staff to prepare them for the patient's arrival. At the completion of the PAT scheduling process, the web site prepares patient handouts describing how to get to the PAT clinic and a medical history form for the patient to fill out. The medical history form also gives the patient an access key so they can fill out the medical history form on-line if they so choose.

Every day, the PAT clinic staff log into the on-line web interface of the system where it provides them with an appointment confirmation call list so they can call patients on the PAT schedule for the next business day so they can confirm their appointment and answer any questions they might have. The staff can enter any comments and the disposition of their call attempts (i.e. confirmed, left message, no answer).

When the patient enters the PAT clinic, the physician can utilize a PAT electronic medical record (EMR) tool or module to look up all available information about the patient. If the patient completed their medical history questionnaire online, that information can be accessed through the physician's PAT EMR module. If the patient did not complete the medical history questionnaire online, the physician or their designee manually enters it into the PAT EMR module. At this point, the physician can determine if the patient needs an EKG. If they do, ancillary staff perform the EKG and electronically transfer it to the PAT EMR module. At this point, the physician examines the patient and uses the tools provided by the EMR module to order the required lab tests and clear the patient for surgery based on the latest evidence based guidelines.

At the end of the visit, the EMR preferably prints a list of lab test prescriptions for the patient along with instructions as to where they can have the testing performed. The patient has their blood drawn and any other required testing completed. In the preferred embodiment, the lab results are automatically sent by the lab electronically to the PAT EMR system via Internet based web services.

Once all the lab tests are back, the PAT physician can: 1) Clear the patient for surgery or 2) Order more follow up tests if the first round of testing revealed significant abnormalities or 3) Cancel the patient's surgery. Once the PAT physician has made the final determination, they mark the visit complete at which point, the system automatically prepares reports that are faxed to the surgery center. These same reports are available to the surgeon's office via www.patclinic.com. The completed visit is also automatically submitted for billing to the patient's insurance carrier.

These and other advantages of the present invention are provided by: a system for scheduling pre-admission testing, comprising: an on-line interface adapted to allow scheduling of pre-admission testing (PAT) and access of PAT reports; a database for storing PAT scheduling information; an electronic module adapted to retrieve information stored on the system including PAT scheduling information, the electronic module also adapted to input patient information for storage in the system; and wherein the system allows users to connect to the on-line interface from remote locations and is adapted to allow surgeons or their offices to schedule PAT appointments and to access said PAT reports through the on-line interface.

In the preferred embodiment, the on-line interface is adapted to allow the input of patient demographic and medical information from a remote location for storage in the system prior to the PAT appointment. The system is preferably adapted to allow retrieval of the patient demographic and medical information from the physician's electronic module. The system is preferably adapted to provide an access key to users for use in inputting patient demographic and medical information from a remote location.

Obvious modifications to the present invention are expected to fall within the scope of the claims of the present invention. The above stated and other advantages of the present invention will be better understood from the following description of the drawings and detailed description of the preferred embodiment(s).

BRIEF DESCRIPTION OF THE DRAWINGS

A better understanding of the present invention will be obtained when reference is made to the accompanying drawings, wherein

FIG. 18 illustrates an example of a completed HPI/Exam screen shot;

FIG. 20 illustrates an example EMR tool screen shot showing completed patient assessment and plan;

DETAILED DESCRIPTION OF A PREFERRED EMBODIMENT

The present system is preferably accomplished through a set of software modules and processes designed to streamline the PAT process for the surgeon, patient, and surgical facility. The software is designed to support multiple surgical specialties and surgical facilities and it is aware of requirements unique to each surgeon and/or surgical facility. The software is used by the PAT clinic to significantly improve the PAT experience for all stakeholders.

Figure 1:
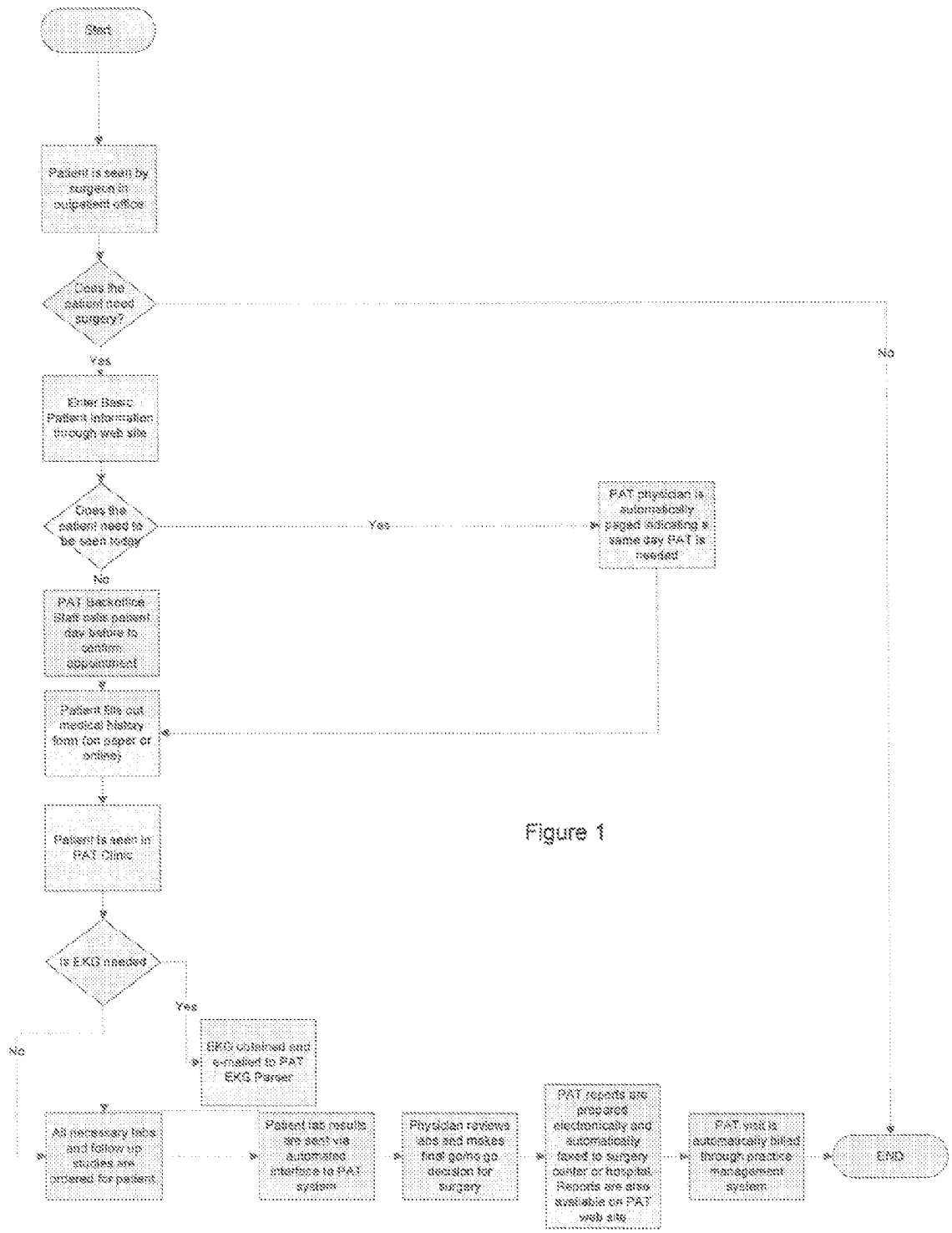
FIG. 1 illustrates a flowchart of one embodiment of the process of the present invention.
Figure 2:
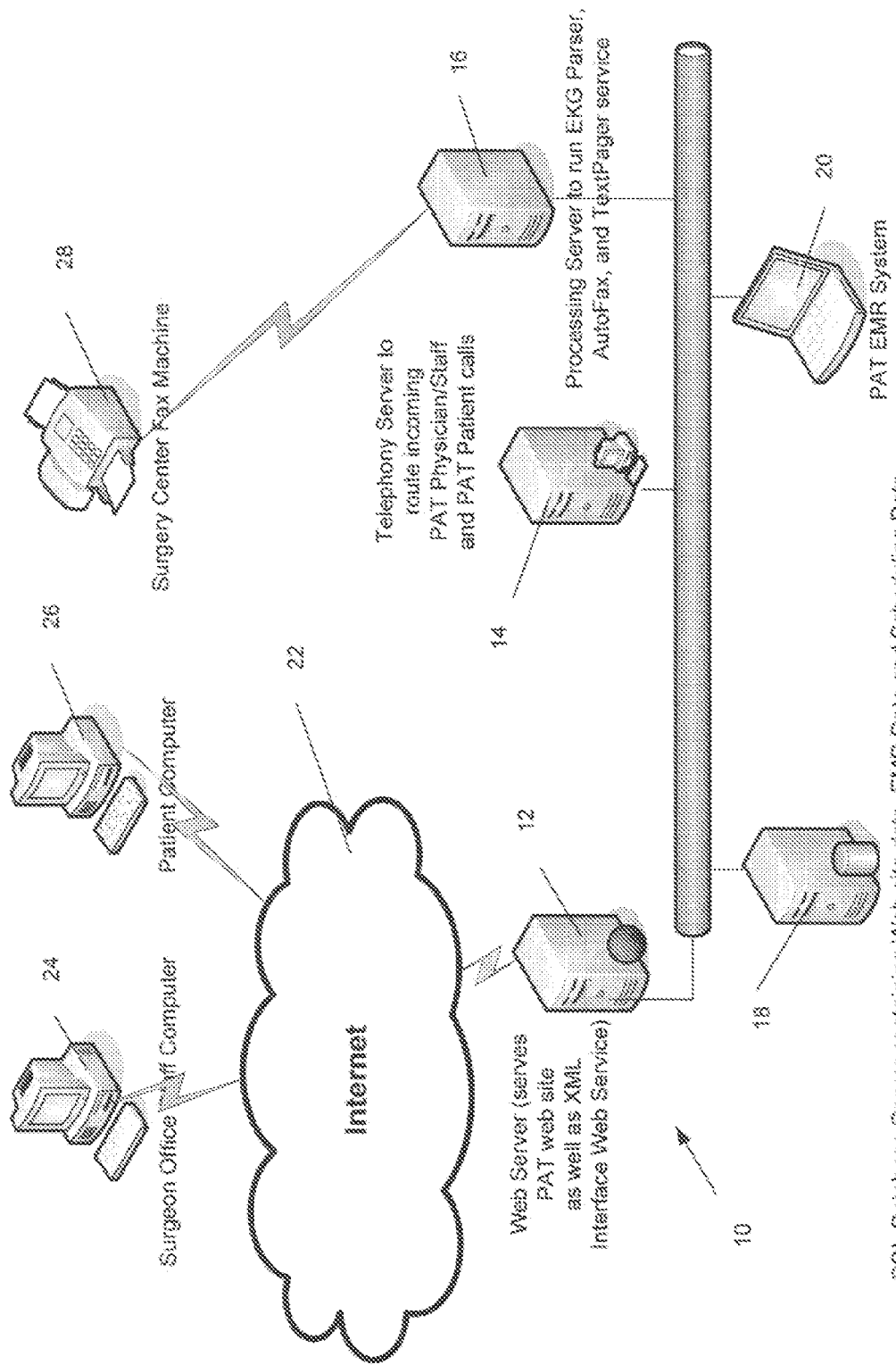
FIG. 2 illustrates a block diagram of one embodiment of the present invention.

FIG. 1 illustrates a flowchart of one embodiment of the process of the present invention. FIG. 2 illustrates a block diagram of one embodiment of the present invention. In one embodiment, the system of the present invention 10 includes a web server 12, a telephony server 14, a processing server 16, a database server 18, and a PAT EMR system 20. The components of the present invention are connected to the Internet 22. The web server of the present invention can be accessed through the Internet by the surgeon's office 24 or the patient's home computer 26. The present invention is also preferably connected to the fax machine of the surgery center 28. Although, in the present invention, the preferred connections are through the Internet, it is also appreciated that other private or virtual networks may be used.

The Web server of the present invention preferably serves the PAT website as well as XML Interface Web Service. The telephony server is used to route incoming PAT physician and PAT patient calls. The processing server is preferably used to run the EKG parser application, the auto-fax application, and the text pager application. The database server may be a SQL server containing website data, EMR data and scheduling data. It is appreciated that the servers of the present invention may be combined or run off the same machine.

Figure 3:
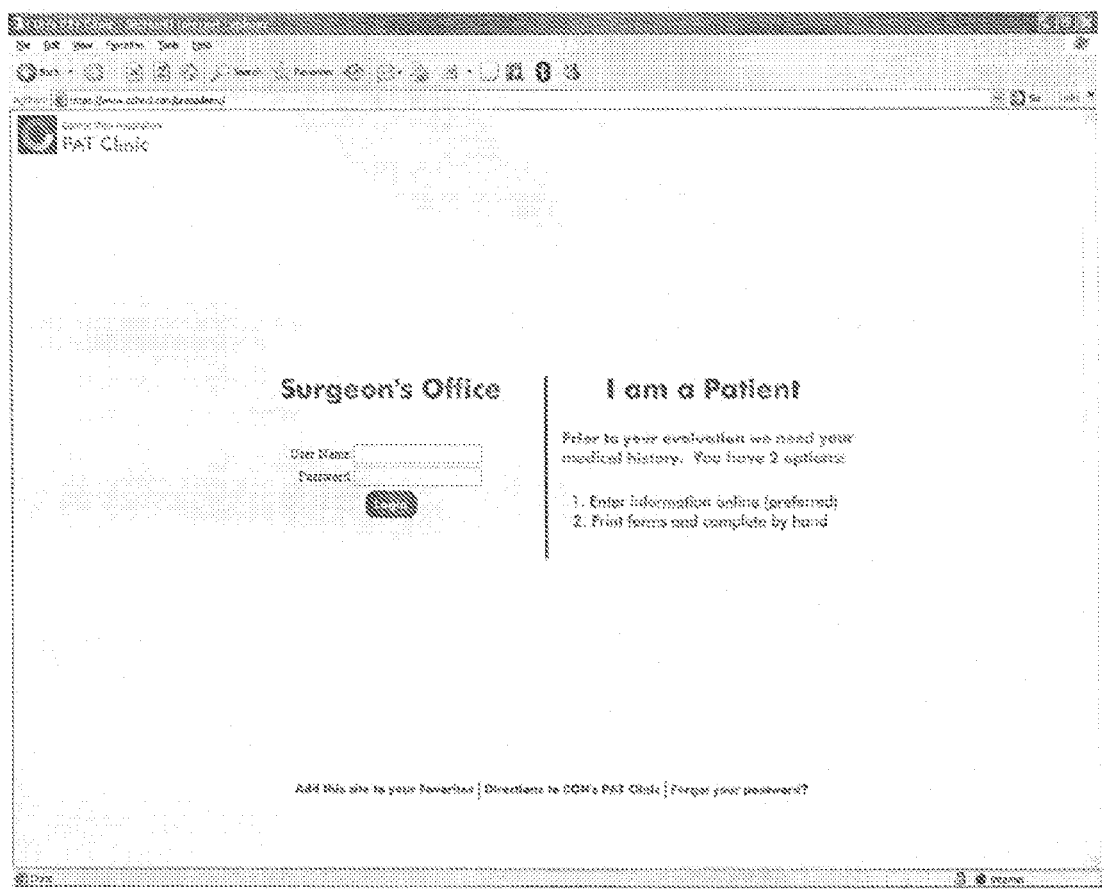
FIG. 3 illustrates one embodiment of the main page of the web interface.

First, when the surgeon decides to schedule a patient for surgery, they preferably go to an on-line web site such as www.patclinic.com to enter basic demographic information about the patient and their surgery as well as schedule a PAT time. FIG. 3 illustrates one embodiment of the main page of the web interface. The surgeon logs-in to access the services of the system. Patients can also obtain medical questionnaire forms to print out or fill-out on-line.

Figure 4:
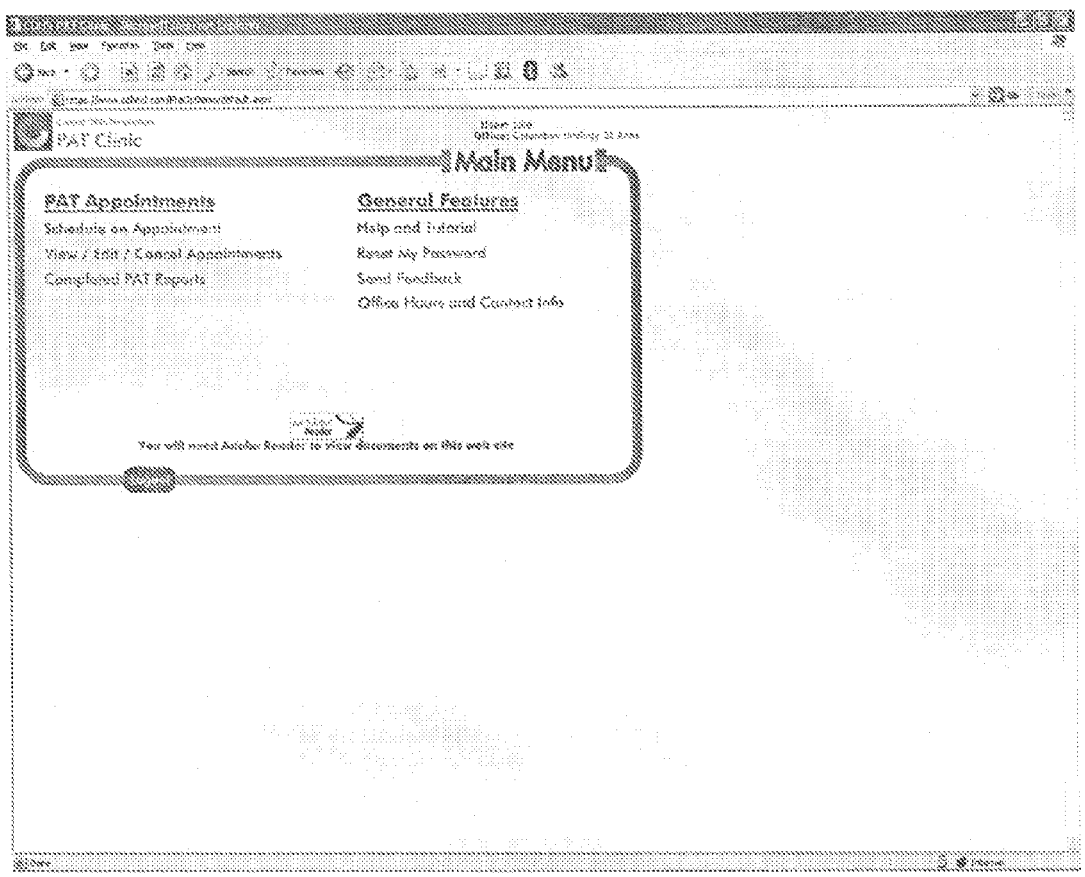
FIG. 4 illustrates one embodiment of the main menu of the on-line or web interface of the present invention.

FIG. 4 illustrates one embodiment of the main menu of the on-line or web interface of the present invention. Through the main menu the surgeon or her office can schedule a PAT appointment, view/edit/cancel appointments or access completed PAT reports. They may also access Help tutorials for the system, reset passwords, send feedback, or check on office hours and contact information.

Figure 5:
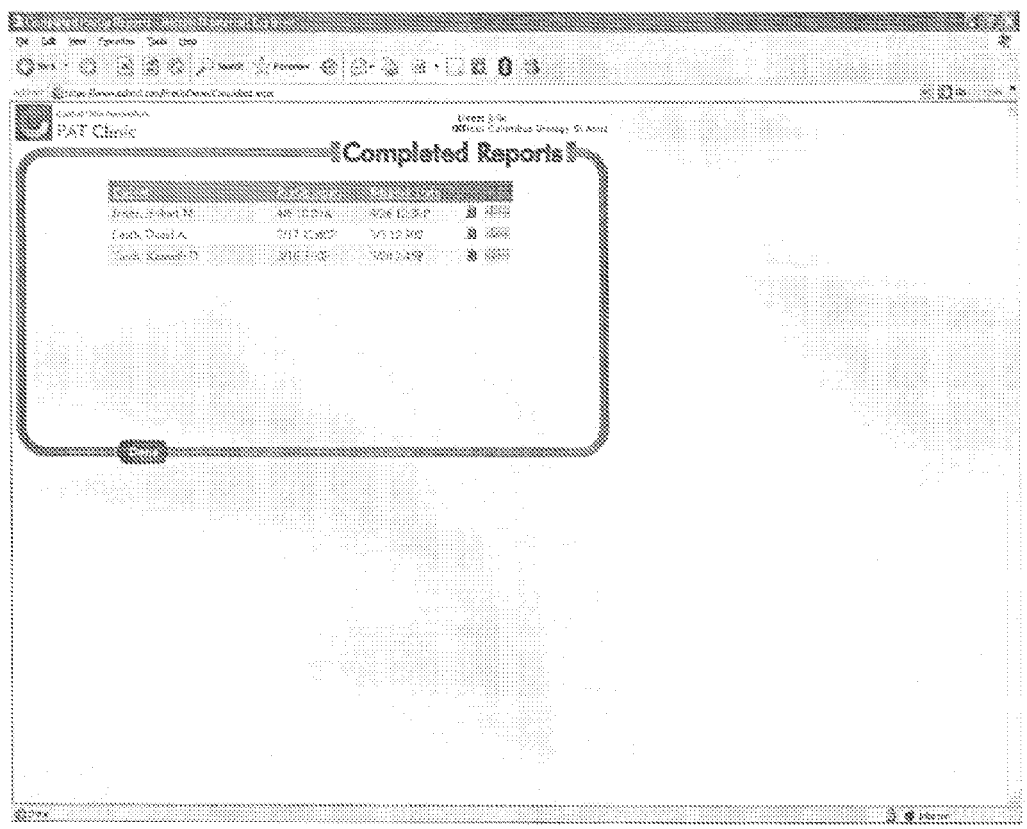
FIG. 5 illustrates one embodiment of the web page of the present system allowing physicians to obtain completed PAT records.

FIG. 5 illustrates one embodiment of the web page of the present system allowing physicians to obtain completed PAT records. In one embodiment, the completed records are automatically generated and made available through the web interface after the PAT physician has completed the report on her EMR tool.

Figure 6:
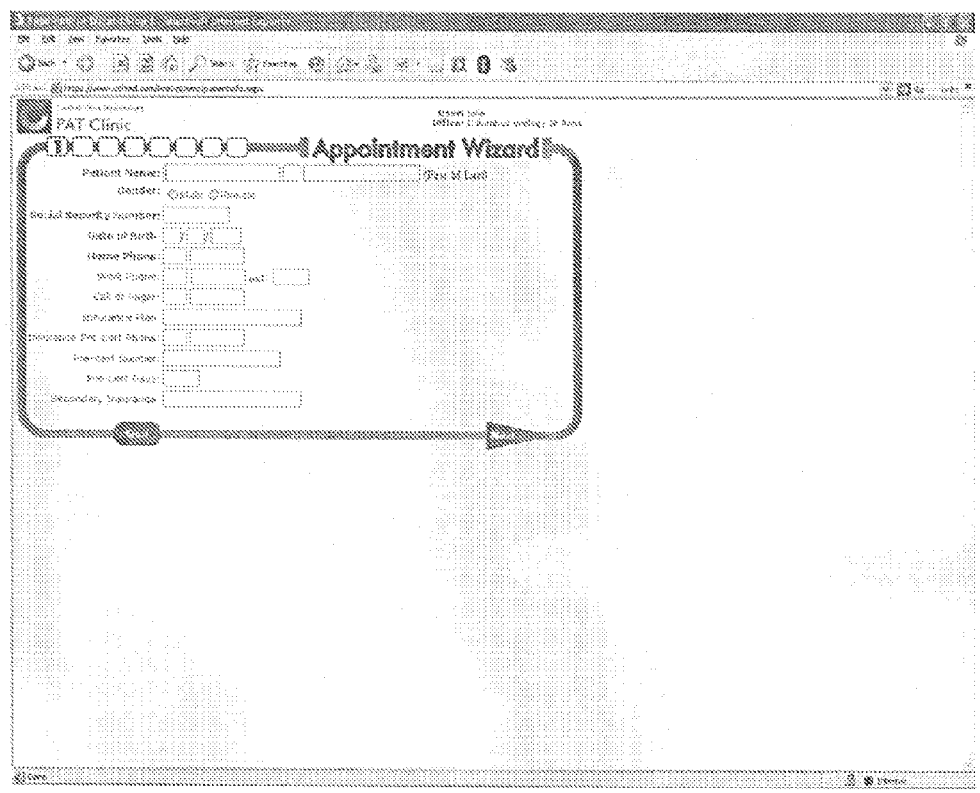
FIG. 6 illustrates one embodiment of the screen shot of the appointment wizard of the present invention.

FIG. 6 illustrates one embodiment of a screen shot of the appointment wizard of the present invention that is used by the surgeon's office to schedule a PAT appointment on-line. The patient's personal information is collected including social security number, contact information and insurance information.

Figure 7:
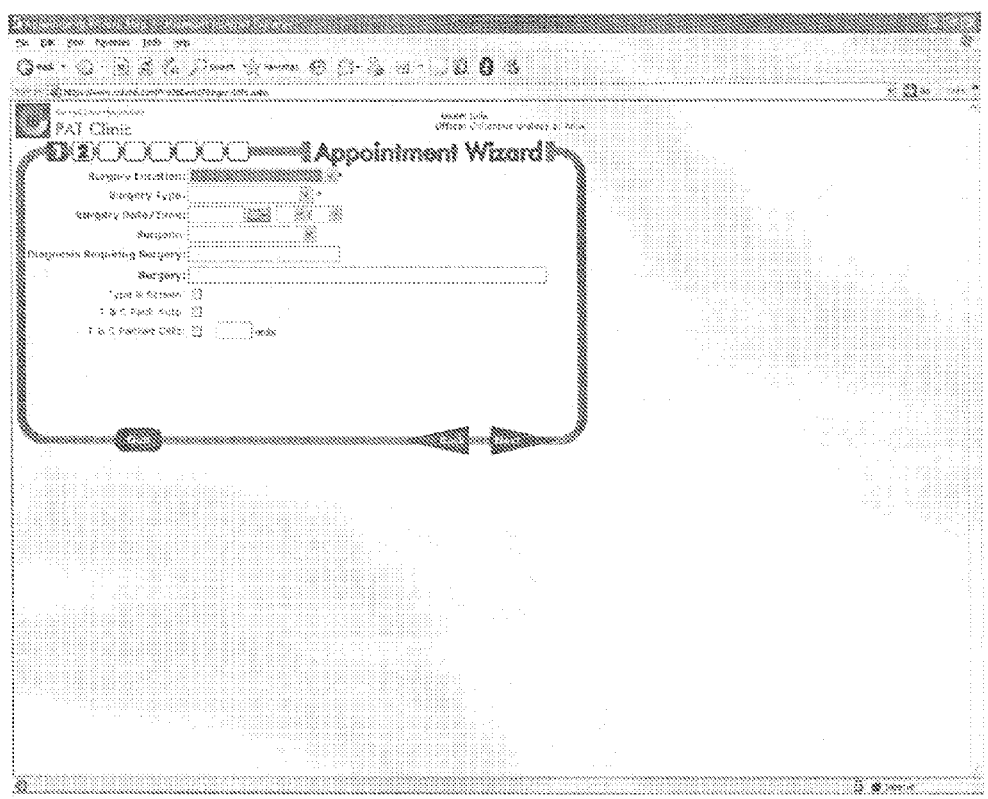
FIG. 7 illustrates one embodiment of a screen shot of another page of the appointment wizard of the present invention.

FIG. 7 illustrates one embodiment of a screen shot of another page of the appointment wizard of the present invention. The surgeon's office preferably enters the surgery location, date and time, surgeon name and other relevant information.

Figure 8:
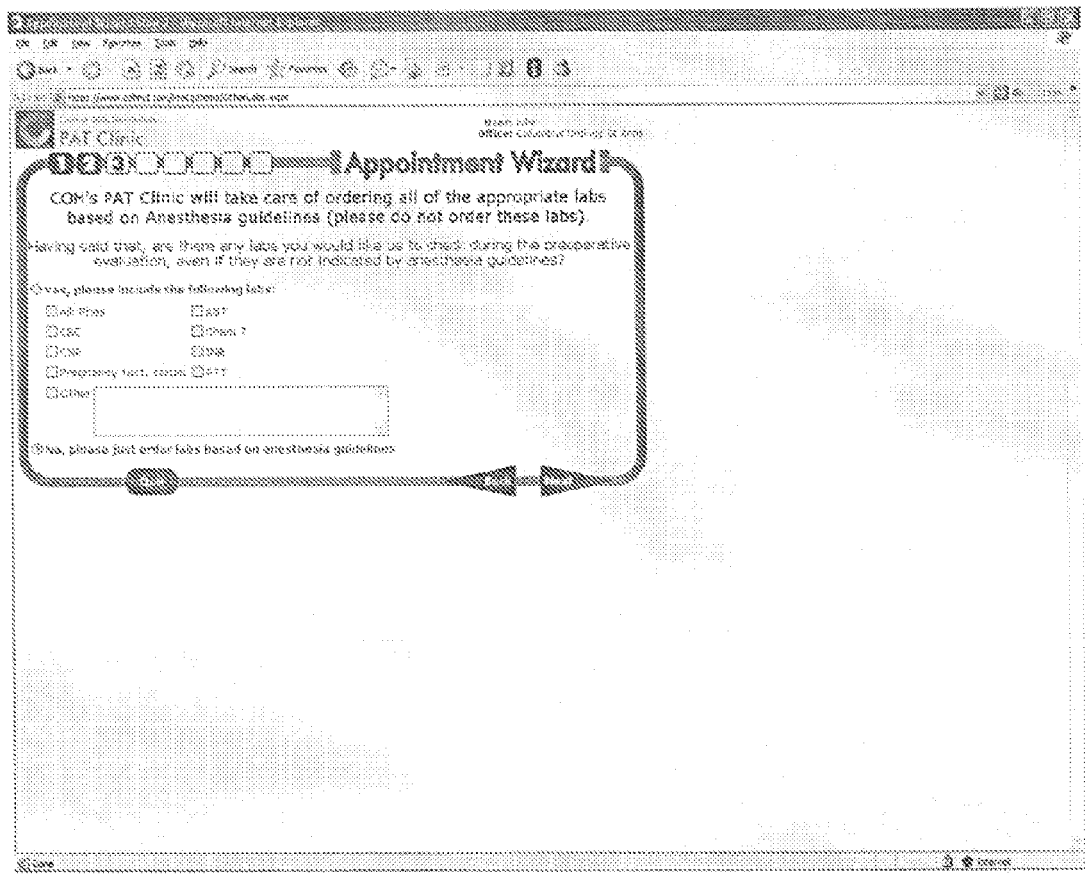
FIG. 8 illustrates one embodiment of a screen shot of another page of the appointment wizard of the present invention.

FIG. 8 illustrates one embodiment of a screen shot of another page of the appointment wizard of the present invention that allows the surgeon's office to order additional labs for the PAT.

Figure 9:
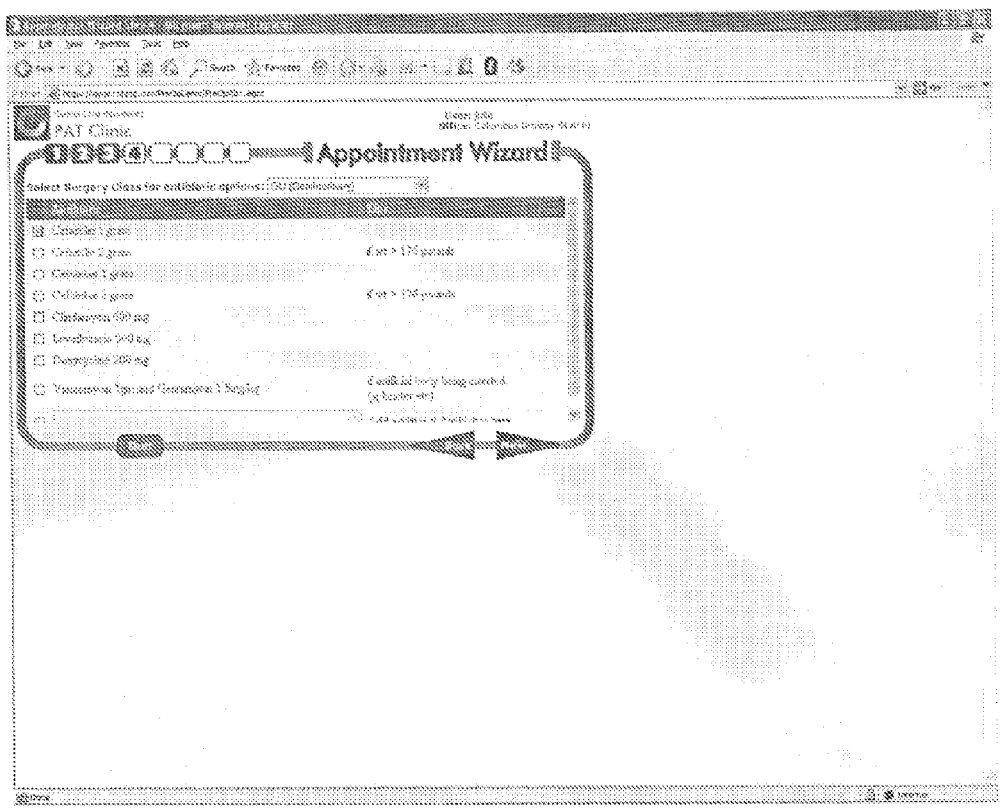
FIG. 9 illustrates one embodiment of a screen shot of another page of the appointment wizard of the present invention.

FIG. 9 illustrates one embodiment of a screen shot of another page of the appointment wizard of the present invention that allows the surgeon's office to indicate preoperative antibiotics.

Figure 10:
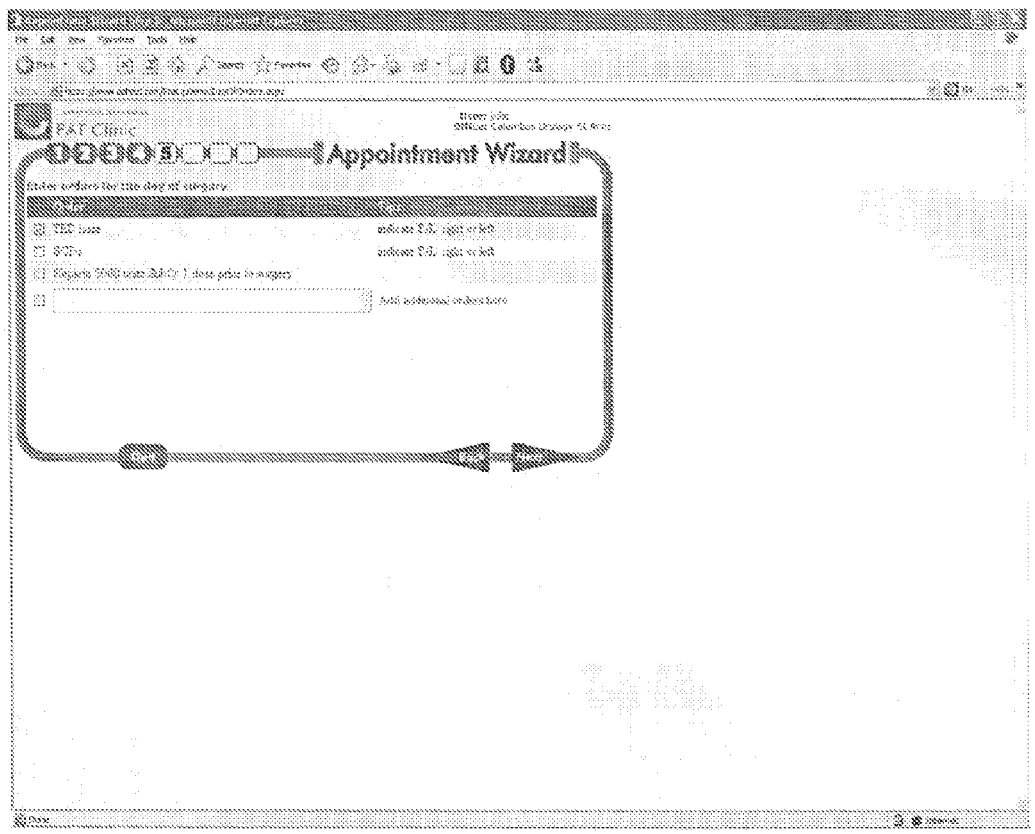
FIG. 10 illustrates one embodiment of a screen shot of another page of the appointment wizard of the present invention.

FIG. 10 illustrates one embodiment of a screen shot of another page of the appointment wizard of the present invention that allows the surgeon's office to enter additional orders for the day of surgery.

Figure 11:
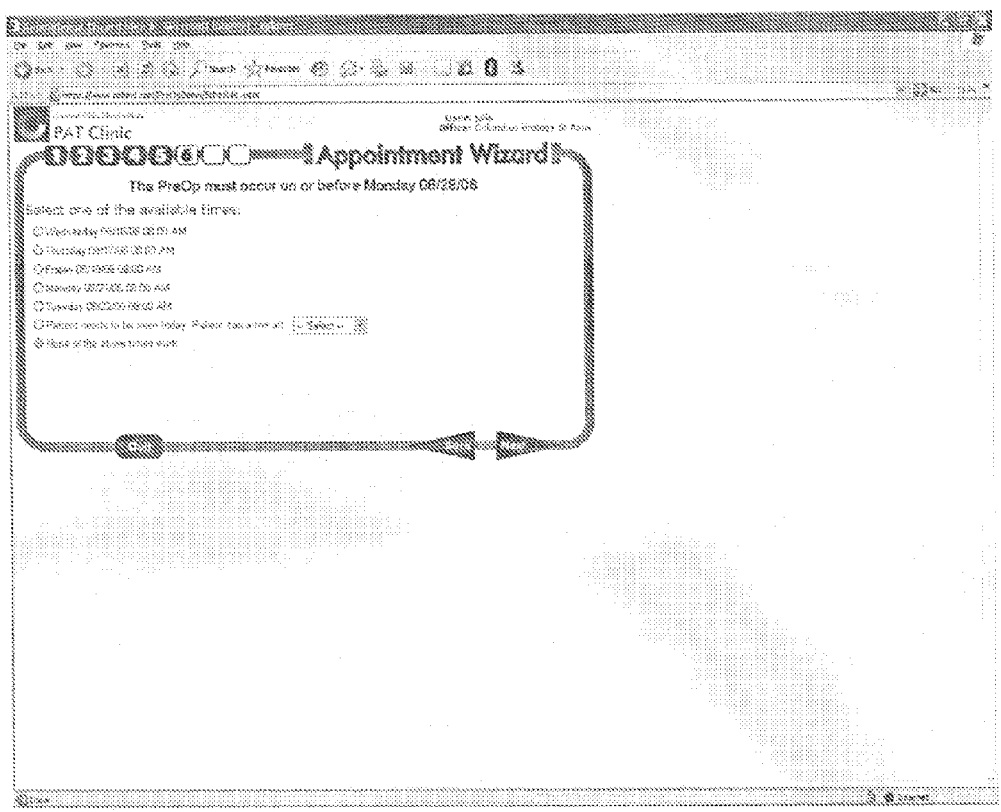
FIG. 11 illustrates one embodiment of a screen shot of another page of the appointment wizard of the present invention.

FIG. 11 illustrates one embodiment of a screen shot of another page of the appointment wizard of the present invention that allows the surgeon's office to schedule a time for the PAT or preop testing. The system preferably uses an algorithm that looks at the surgery date, the current date and obtains a range of valid days and times for the appointment. Preferably, the times that are provided are adjacent to other PAT appointments already scheduled so that the physician can do appointments back to back if possible. The interface provides options to schedule a PAT appointment on other days or times or an option to schedule the appointment for that day.

Figure 12:
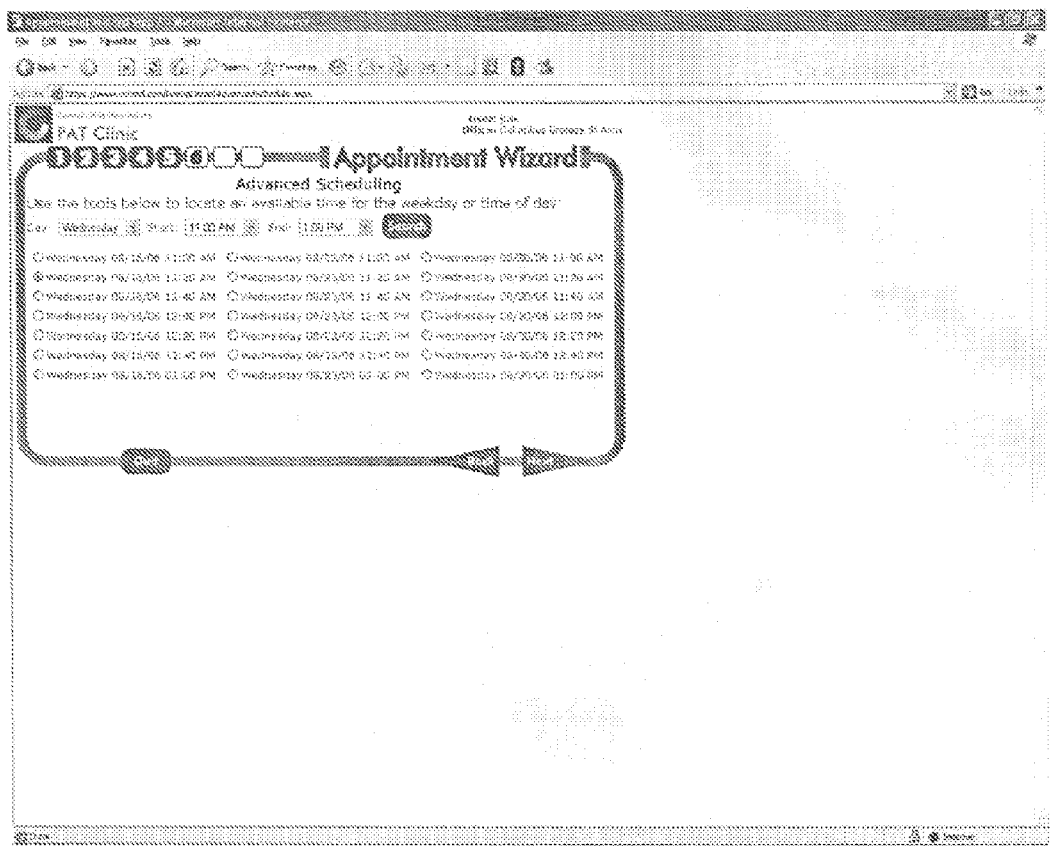
FIG. 12 illustrates on embodiment of a screen shot of the advanced scheduling screen of the present invention.
Figure 13:
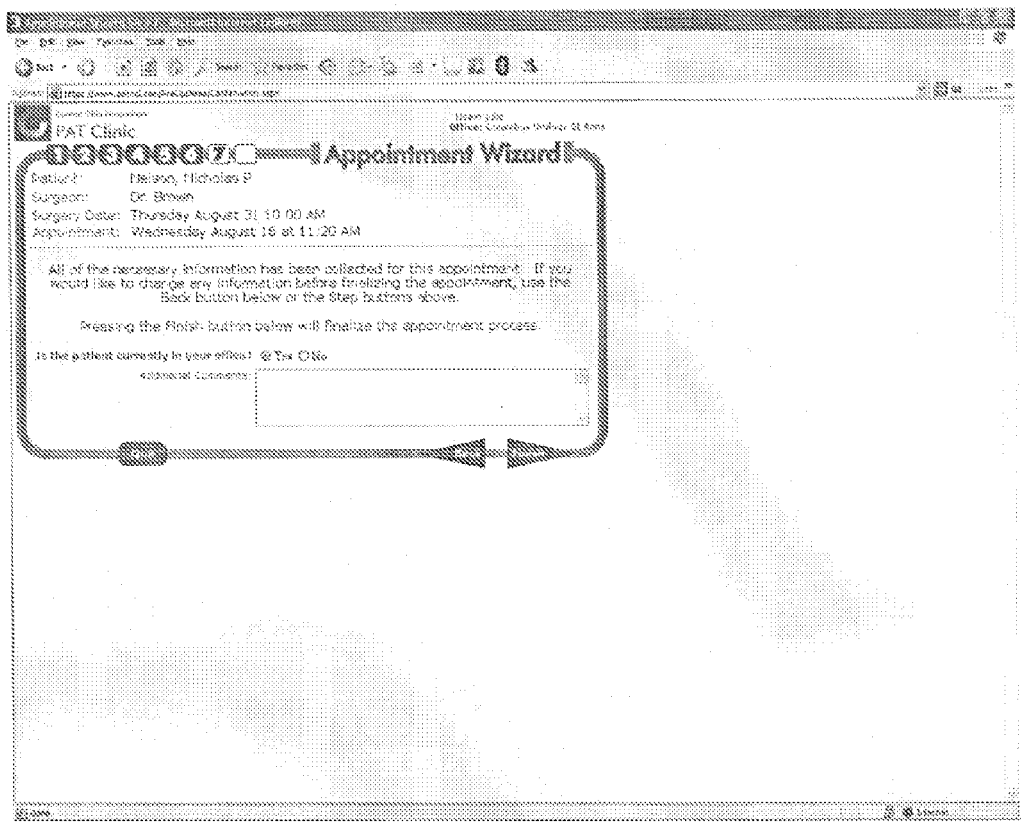
FIG. 13 illustrates one embodiment of the appointment confirmation screen of the present invention.
Figure 14:
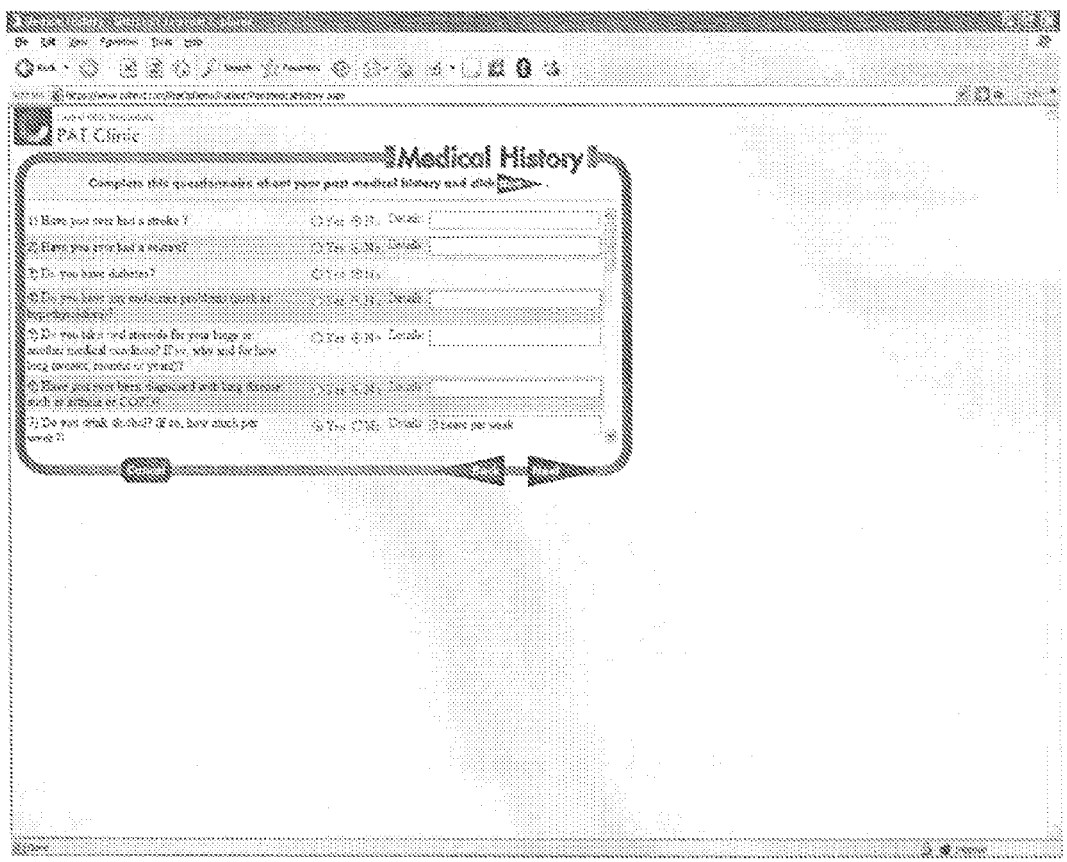
FIG. 14 illustrates an example of a portion of a medical history questionnaire.

FIG. 12 illustrates on embodiment of a screen shot of the advanced scheduling screen of the present invention. FIG. 13 illustrates one embodiment of the appointment confirmation screen of the present invention. In the preferred embodiment, the user scheduling the appointment is asked if the patient is currently in the office. If the answer is "yes", the system provides patient handouts describing how to get to the PAT clinic and a patient medical history questionnaire. The patient is also provided an access key so they can fill out the medical history form on-line if they so choose. FIG. 14 illustrates an example of a portion of a medical history questionnaire.

In some cases, the PAT must be done that day (i.e. the patient is from out of town and doesn't want to make a special trip back or the surgery is scheduled within the next few days). If the PAT must be done the same day, the system is programmed to page (e.g., text page) the PAT physician and ancillary staff to prepare them for the patient's arrival.

The PAT clinic staff logs into the web server through the web interface (e.g., www.patclinic.com) where it provides them with an appointment confirmation call list so they can call patients on the PAT schedule for the next business day so they can confirm their appointment and answer any questions they might have. The staff can enter any comments and the disposition of their call attempts (i.e. confirmed, left message, no answer).

Figure 15:
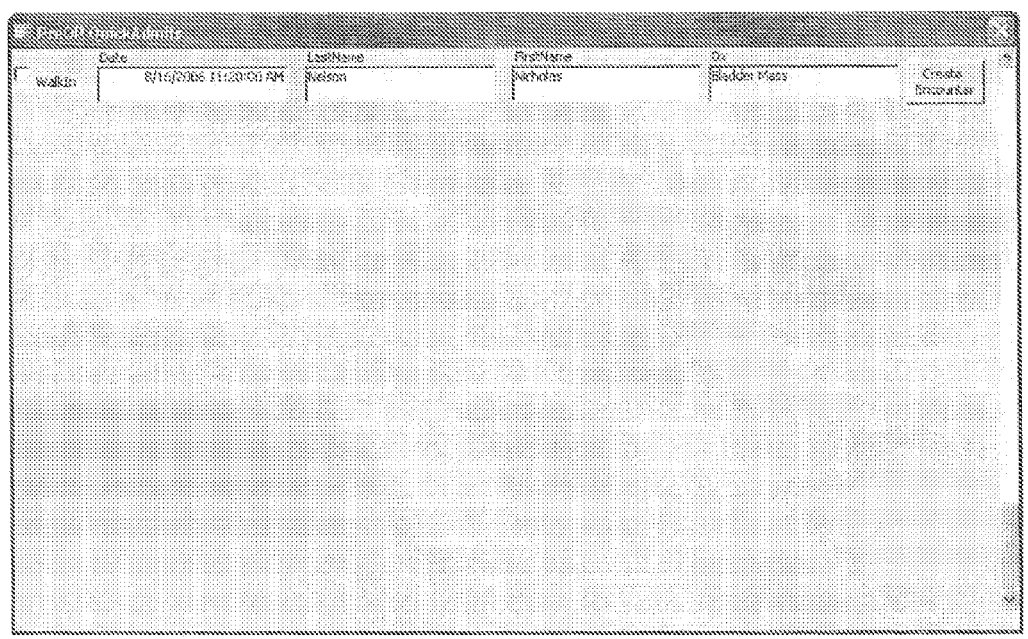
FIG. 15 illustrates one example of a screen shot from a physician EMR module showing pending PAT patients.

When the patient enters the PAT clinic, the physician can utilize an electronic medical record (EMR) tool or module to look up all available information about the patient. The EMR tool is a software application or module loaded on a mobile computing platform, such as a personal computer, that a PAT or other rounding physician uses to access and update admission queues and patient records stored in the database server and possibly other information stored in hospital records. The physician's mobile computing platform may connect to the system of the present invention via a wired or wireless network connected to the Internet. The PAT physician(s) can then receive the updated information via synchronization through their EMR tools, e.g., using SQL Server replication functionality over a secure Internet connection (which may be wired or wireless) to obtain the patient information. FIG. 15 illustrates one example of a screen shot from a physician EMR module showing pending PAT patients.

Figure 16:
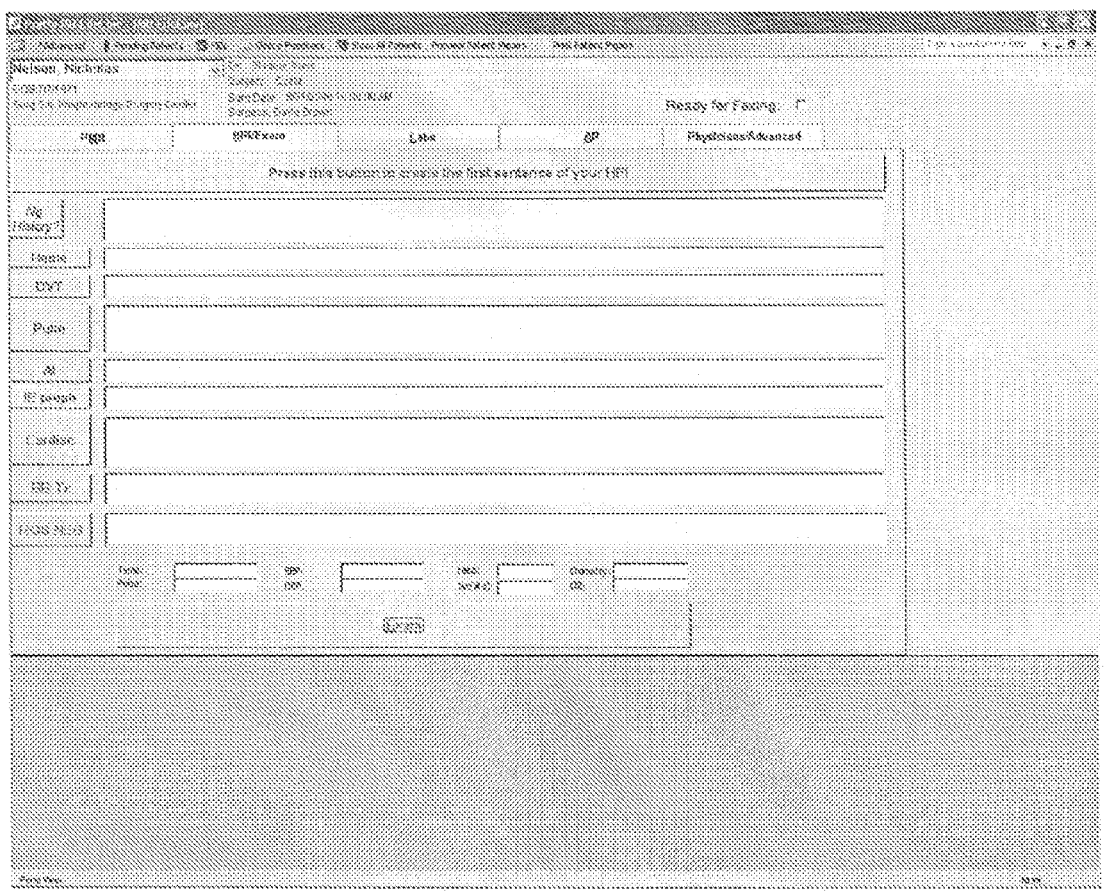
FIG. 16 illustrates an example screen shot of a patient's medical history displayed on a physician's EMR.
Figure 17:
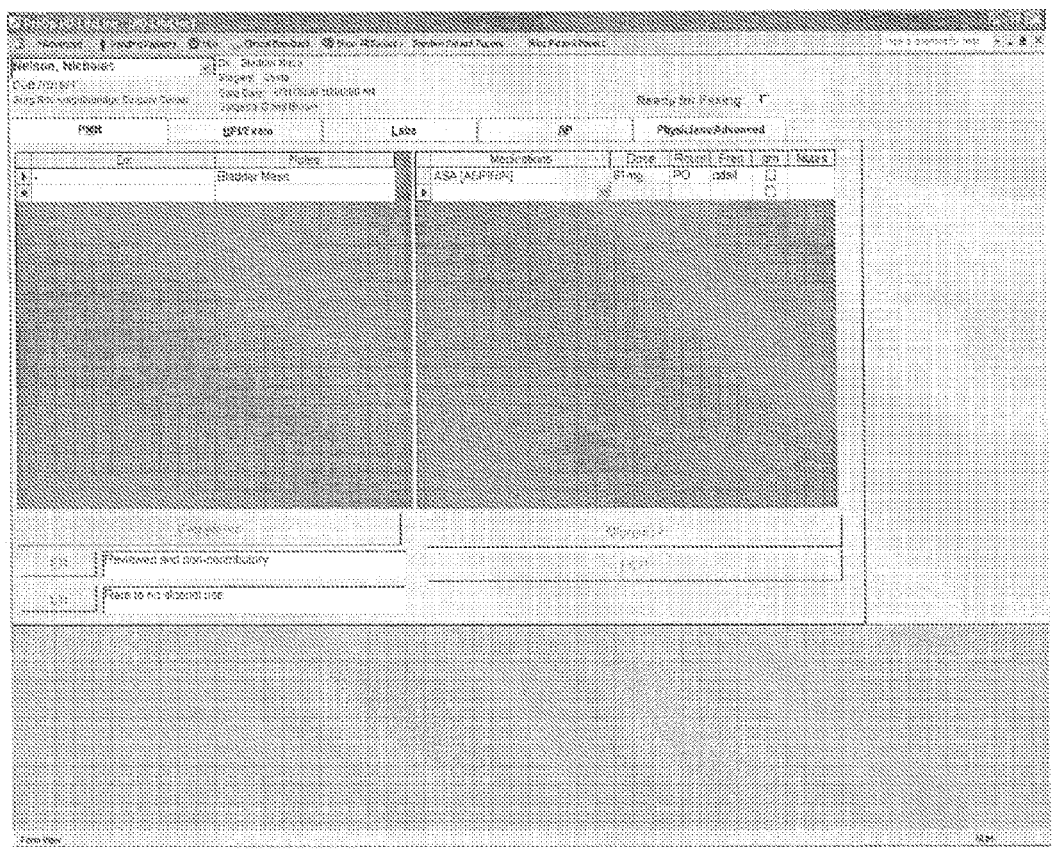
FIG. 17 illustrates an example screen shot of a patient's past medical history information displayed on a physician's EMR tool.

FIG. 16 illustrates an example screen shot of a history of present illness (HPI)/examination information displayed on a physician's EMR tool. FIG. 17 illustrates an example screen shot of a patient's past medical history information displayed on a physician's EMR tool. If the patient completed their medical history questionnaire online, that information is available through the PAT EMR module. If the patient did not complete the medical history questionnaire online, the physician or their designee manually enters it into the PAT EMR module.

Figure 18:
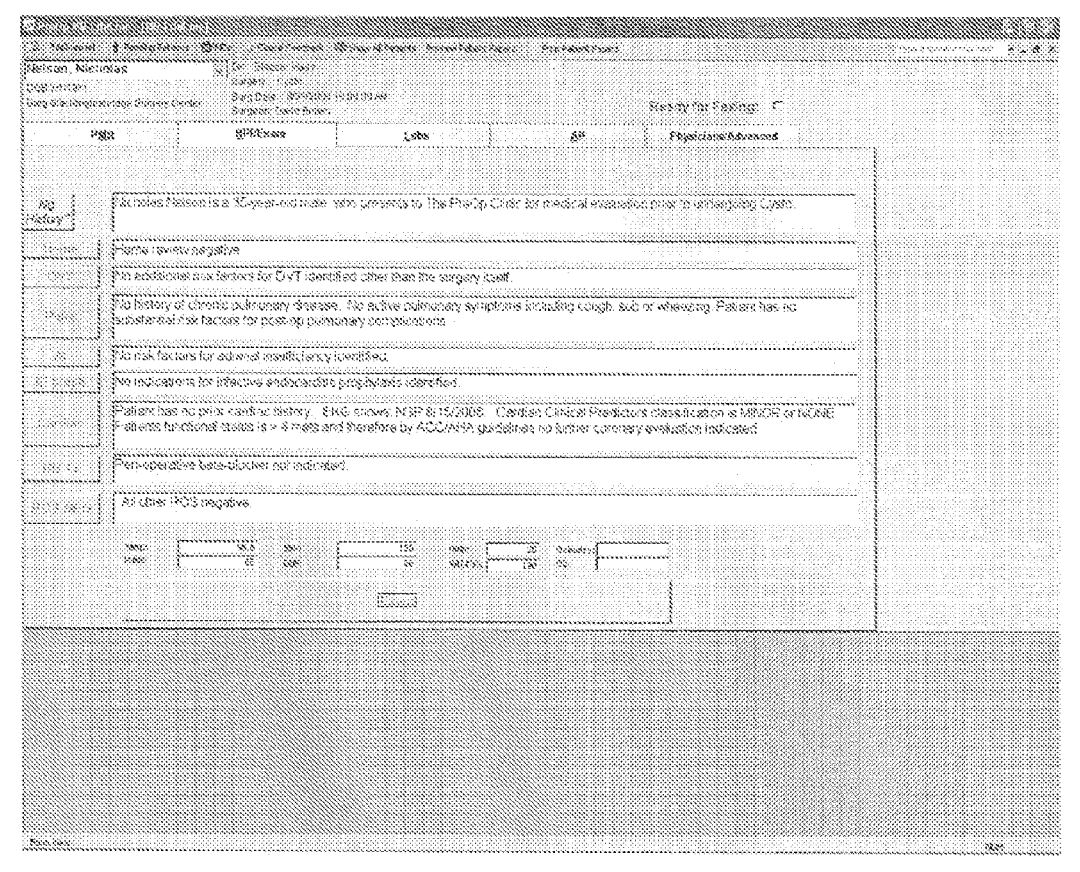

FIG. 18 illustrates an example of a completed HPI/Exam screen shot. This screen is preferably filled out by the PAT physician during their initial encounter and examination of the patient during the PAT visit.

Figure 19:
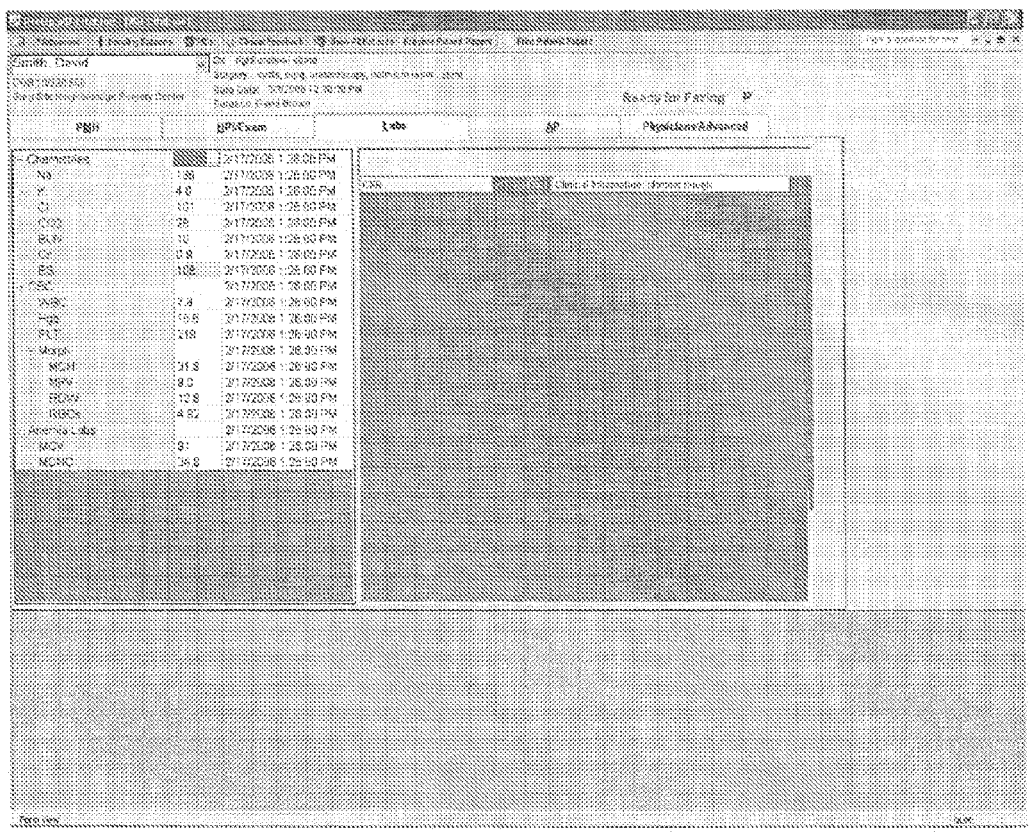
FIG. 19 illustrates a sample EMR tool screen shot used to view lab test results for the patient.

At this point, the physician can determine if the patient needs an EKG. If they do, ancillary staff perform the EKG and electronically transfer it to the PAT EMR module. At this point, the physician examines the patient and uses the tools provided by the EMR module to order the required lab tests and clear the patient for surgery based on the latest evidence based guidelines. FIG. 19 illustrates a sample EMR tool screen shot used to view lab test results for the patient (these lab results generally are not available until after the examination, the PAT physician returns to this screen after the lab results are received.)

Figure 20:
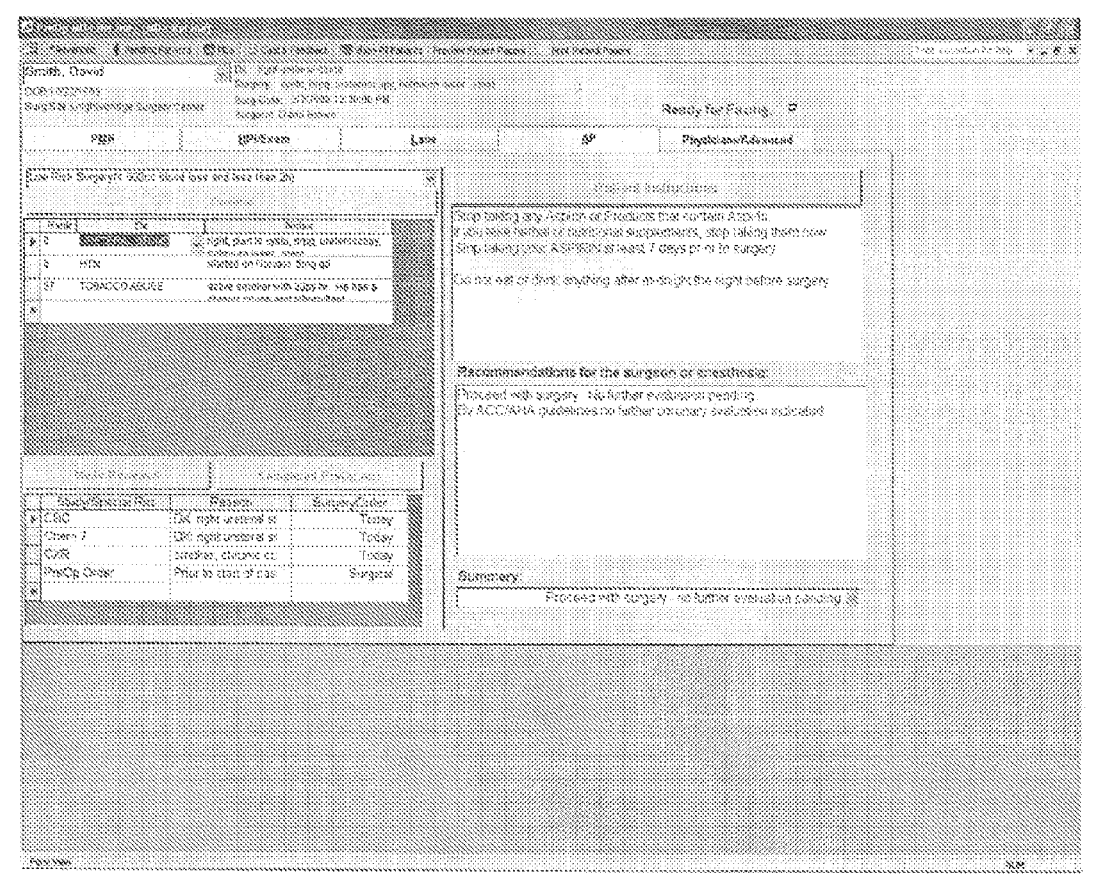

FIG. 20 illustrates an example EMR tool screen shot showing completed patient assessment and plan.

At the end of the visit, the EMR prints a list of lab test prescriptions for the patient along with instructions as to where they can have the testing performed. The patient has their blood drawn and any other required testing completed. In the preferred embodiment, the lab results are automatically sent by the lab electronically to the PAT EMR system via Internet based web services.

Figure 21:
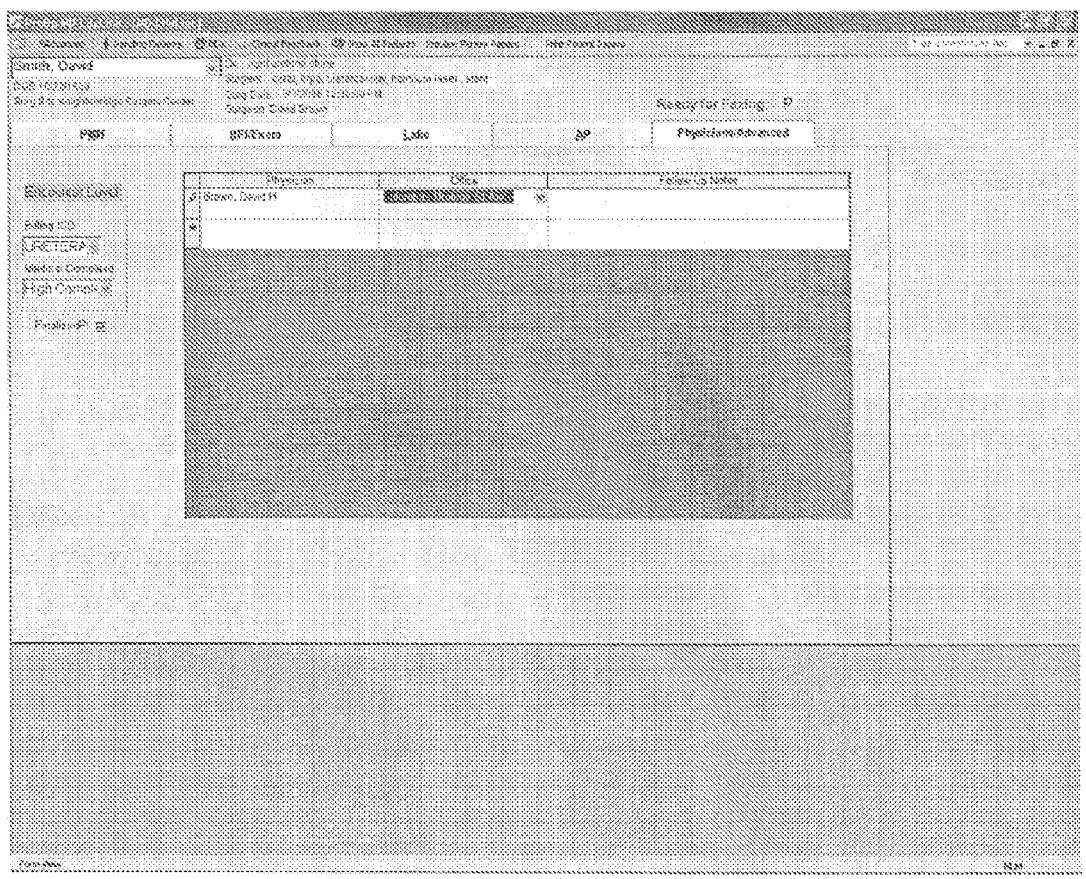
FIG. 21 illustrates an example of an EMR screen shot showing the "Completed Physicians/Advanced Tab.

Once all the lab tests are back, the PAT physician can: 1) Clear the patient for surgery or 2) Order more follow up tests if the first round of testing revealed significant abnormalities or 3) Cancel the patient's surgery. Once the PAT physician has made the final determination, they mark the visit complete at which point, the system automatically prepares reports that are faxed to the surgery center. FIG. 21 illustrates an example of an EMR screen shot showing the "Completed Physicians/Advanced Tab". These same reports are available to the surgeon's office via the Internet by accessing the web interface (e.g., www.patclinic.com). The system is also preferably programmed to automatically submit the visit for billing to the patient's insurance carrier.

In the preferred embodiment, the present system utilizes a Microsoft SQL Server database engine as its data repository. In the preferred embodiment, most of the modules are written with Microsoft's Visual Studio 2005 development package (utilizing Visual Basic.NET and ASP.NET). The EMR portion of the system is preferably written using Microsoft Access (while still using Microsoft SQL Server as the Database Engine). The modules can communicate with each other by saving their state information in the SQL Server database.

Modules: service web site—This web site allows the surgeon's office to:

1) Schedule a new PAT clinic appointment for a patient
2) Reschedule/Cancel existing PAT clinic appointments
3) View completed PAT clinic reports It allows a patient to: 1) print forms to complete by hand; and 2) complete the medical history form online if desired. It allows PAT clinic office staff to: 1) confirm PAT clinic appointments and 2) review completed PAT clinic reports.

AutoFax Service. The autofax service looks for completed PAT clinic encounters and automatically prepares and faxes reports and forms required by the patient's surgical facility. It can also fax reports to other physicians that the PAT clinic physician entered.

EKGListener. This program listens via Simple Mail Transfer Protocol (SMTP) for new EKG e-mails sent by the EKG machine. When it receives an EKG, it strips it to a file for parsing by the EKGParser.

Figure 22:
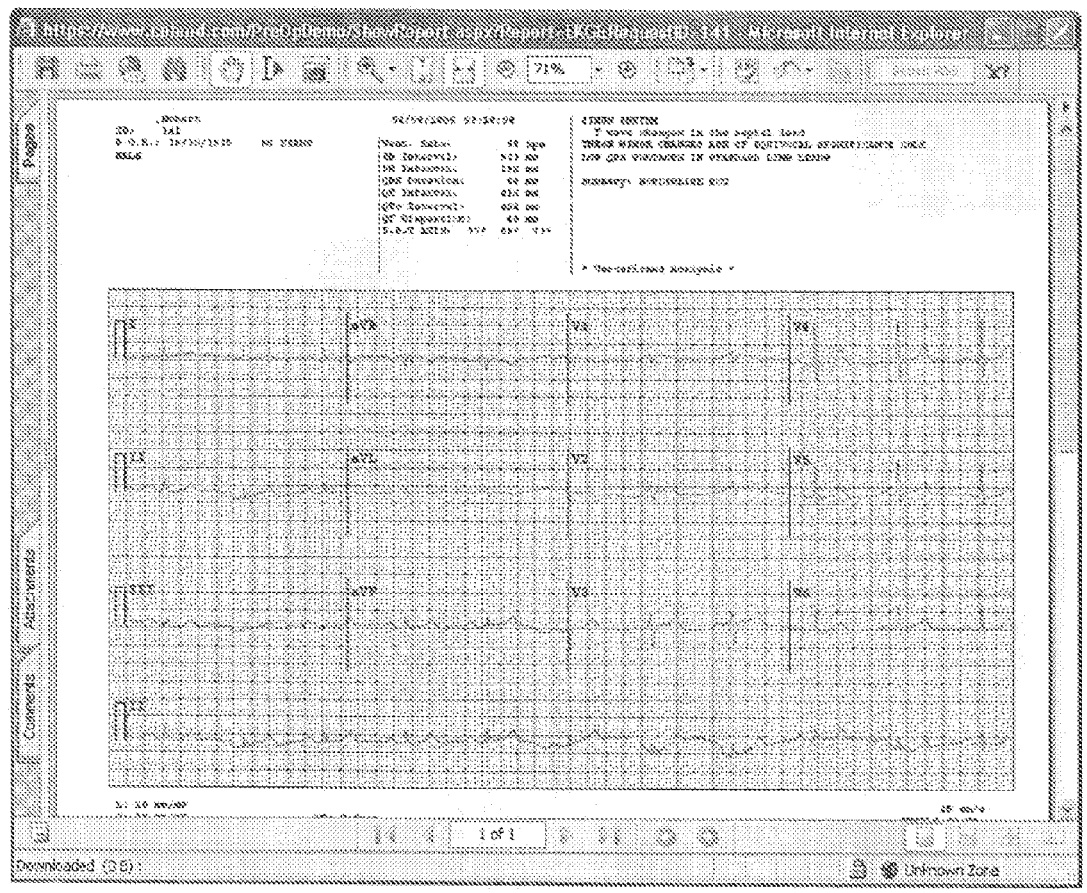
FIG. 22 illustrates an example of an EKG screen shot captured by EKGParser.

EKGParser. This program parses e-mails received by the EKGListener to attach them to the proper patient and record them in a format readable by the PAT EMR tool as well as the www.patclinic.com web site and autofax service. FIG. 22 illustrates an example of an EKG screen shot captured by EKGParser.

Telephony Tie In. The telephony server enables a dedicated PAT clinic hotline for patients, referring surgeons, and surgical facility staff. The menu is designed to route the caller to the PAT physician, PAT office staff, or PAT technical staff based on the nature of the call.

Backoffice Billing Tie In. Once the visit is marked complete by the physician in the EMR tool, it is automatically available to the billing software module that automatically bills the right entity.

XML Lab Interface Web Service. Any labs ordered by the PAT physician are usually completed by a lab that can automatically send the results directly into the EMR system via an XML web service available on the Internet.

Physician's PAT EMR tool. This program is what the physician uses to see the patient in the PAT clinic. It may reside on any appropriate computing platform such as a laptop computer or handheld processor. It contains all available demographic and medical history information entered through www.patclinic.com. In the preferred embodiment, the EMR screens contain the demographic and medical history information, and the information is stored in the Microsoft SQL Server database. It is also aware of the surgical facility's testing requirements so that the all of the proper labs are ordered for the patient to avoid a costly same day surgery cancellation. It is also updated with all the latest evidenced based guidelines for preoperative clearances. The algorithms aid the physician in determining any follow up testing and the patient's medical clearance status. It enables the physician to review the patient's lab results to make a final determination on the patient's surgical status.

The PAT EMR module is preferably designed to provide the PAT physician with a list of pending PAT patients for the day (as well as display any same day PAT appointments that are scheduled). Once a patient shows up to the office for their appointment, the nurse or technician checks the patient into an exam room. The PAT physician verifies the patient's medical history (which was either entered online through www.patclinic.com, or provided in writing via the medical history form, or provided orally by the patient during the exam). The medical history includes any medical conditions the patient currently has, any allergies the patient has, and any current medications the patient is taking.

The EMR provides fields for the physician to document the history of present illness, family history, social history, as well as examine and review the patient's major organ systems. The EMR system helps the physician identify any risk factors the patient might have in the areas of cardiac, deep vein thrombosis (blood clots), pulmonary, adrenal insufficiency, infective endocarditis, or the need for beta blocker therapy. The EMR utilizes the latest evidence based medical studies to assist the physician in determining if any further workup or medical therapy is needed before the patient can proceed to surgery.

The physician documents significant medical issues that are pertinent to the patient's surgery in the Assessment and Plan (AP) section. Here the physician can also order lab tests that need to be completed before the patient can be cleared for surgery. The system will automatically recommend some lab tests based on the patient's medical history, current surgery, age, and gender to comply with the surgery center or hospital's requirements for testing before surgery. The physician can also alter the patient's current medical therapy to prepare them for their surgery (i.e. stopping blood thinners, starting beta blocker therapy, etc).

Once the patient has completed the required lab testing (and any other testing the PAT physician ordered, such as stress tests or cardiology consults), the physician can review the lab results in the lab page. If all of the testing comes back okay, the PAT physician marks the patient as ready for surgery, otherwise, the PAT physician can cancel the surgery or order additional testing.

The Physicians/Advanced section allows the PAT physician to bill the encounter, as well as mark any other physicians associated with this patient so that they can be faxed a copy of the PAT report.

It is thought that the advantages of the present invention will be apparent from the description of the drawings and the preferred embodiments contained herein. It will be appreciated that after reading this specification those skilled in the art will arrive at various modifications to the invention described herein and these modifications are anticipated to fall within the scope of the present invention and the claims contained herein.

What is claimed is:

1. A computerized system for scheduling pre-admission testing comprising:

a database for storing scheduling information for a variety of available and unavailable pre-admission test (PAT) appointments; and one or more servers, connected to a public network, adapted to:

receive from a remote computer a request to schedule a pre-admission test for a patient;

transmit to said remote computer a request to provide patient information for the patient requiring a pre-admission test;

receive from said remote computer the requested patient information;

generate a list of valid available pre-admission test appointments for the patient from pre-admission testing scheduling data electronically retrieved from the database;

transmit the list of valid available pre-admission test appointments for display by the remote computer;

prompt the remote computer to select an appointment from those provided on the list of available appointments that is to be scheduled for the patient;

receive a request from the remote computer to schedule the patient for an appointment that has been selected from the list of available appointments;

update the database to indicate that the patient is scheduled for the selected appointment and that the selected appointment is no longer available;

transmit an appointment confirmation message for display by said remote computer;

receive a request from a remote computer to view a master schedule of all scheduled pre-admission tests for a given testing facility;

compile the master schedule of all scheduled pre-admission tests for a given testing facility;

transmit the master schedule of scheduled pre-admission tests for display by the requesting remote computer;

receive from a remote computer a request to view a list of at least one lab test that must be performed on the patient during pre-admission testing to clear the patient for an upcoming medical procedure;

generate a list of at least one lab test that must be performed on the patient during pre-admission testing based on the received patient information;

transmit the generated list of at least one lab test to the remote computer for viewing;

receive from the remote computer a request to amend the list of at least one lab test by adding at least one lab test to the list;

amend the list of at least one lab test that must be performed on the patient during pre-admission testing by adding at least one lab test to the list; and transmit the amended list of lab tests to the database.

2. A system according to claim 1, further comprising:
a remote computer comprising an electronic module where said remote computer is in electronic communication with said one or more servers and can transmit information to and receive information from said one or more servers.

3. The system according to claim 2, wherein said electronic module is adapted to generate orders for lab tests for the patient, transmit the orders to the labs where said tests will be performed, receive the results from said lab tests, and transmit said results for viewing.

4. A system according to claim 2, wherein said one or more servers is further adapted to:
receive an access key from a remote computer;
validate the access key; and
permit access to certain data stored in the database based on the validation of the access key.

5. A system according to claim 2, wherein said one or more servers is further adapted to accept instructions from said electronic module to fax reports to a facility where the patient is scheduled to have an upcoming medical procedure.

6. A system according to claim 2, wherein said electronic module is adapted to send an electronic signal to a printer where said signal causes the printer to print a list of lab tests or medication prescriptions for the patient.

7. A system according to claim 2, wherein said electronic module is adapted to allow the remote computer to clear patients for surgery following PAT appointments and transmit notice of cleared patients to a remote computer of a facility where the patient is scheduled to undergo an upcoming medical procedure.

8. A system according to claim 2, wherein said electronic module is an Electronic Medical Record (EMR) module loaded on a processing platform.

9. A system according to claim 2, wherein said electronic module is adapted to transmit input collected patient information from the scheduled PAT appointment to the database for storage.

10. A system according to claim 1, wherein said one or more servers is further adapted to page a PAT physician if the scheduled PAT appointment must be done on the same day.

11. A system according to claim 1, wherein said database stores PAT reports and is adapted to allow users to access said PAT reports through said one or more servers.

12. A system according to claim 1, wherein said one or more servers is further adapted to:
accept lab reports electronically;
transmit said reports to the database for storage;
receive requests from a remote computer to view said lab reports; and
transmit said lab reports to the remote computer for viewing.

13. A system according to claim 1, wherein said one or more servers is further is adapted to:
generate the master schedule of all scheduled pre-admission tests every day.

14. A system according to claim 1, wherein said one or more servers is further adapted to:
accept an EKG report electronically;
transmit said EKG report to the database;
receive a request by a remote computer to access said EKG report; and
transmit said EKG report to said remote computer for viewing.

15. A system according to claim 14, wherein said one or more servers is further adapted to automatically attach the EKG report to a corresponding patient record stored in the database.

16. A system according to claim 1, wherein said one or more servers is further adapted to allow surgeons to access information stored in said database remotely by inputting login credentials at a remote computer and transmitting said credentials from said remote computer to said one or more servers.

17. A system according to claim 16, wherein said one or more servers is further adapted to allow surgeons or their offices to enter orders for the day of surgery.

18. A system according to claim 1, wherein said patient information comprises the date of an upcoming surgical procedure scheduled to be performed on said patient and wherein said list of valid available pre-admission test appointments is generated by said one or more servers by comparing the date of the upcoming surgical procedure with the date on which the one or more servers generates said list of valid available pre-admission test appointments.

19. A system according to claim 1, wherein said one or more servers is further adapted to:
receive a request from a remote computer to alter the master schedule of all scheduled pre-admission tests for a given testing facility in a specified manner;

alter the master schedule of all scheduled pre-admission tests for a given testing facility in the manner specified in said request; and transmit the altered master schedule to the database for storage.

20. A computerized system for scheduling pre-admission testing, comprising:

a database for storing scheduling information for a variety of available and unavailable pre-admission test (PAT) appointments; and one or more servers, connected to a public network, adapted to:

receive from a remote computer a request to schedule a pre-admission test for a patient;

transmit to said remote computer a request to provide patient information for the patient requiring a pre-admission test;

receive from said remote computer the requested patient information;

generate a list of valid available pre-admission test appointments for the patient from pre-admission testing scheduling data electronically retrieved from the database;

transmit the list of valid available pre-admission test appointments for display by the remote computer;

prompt the remote computer to select an appointment from those provided on the list of available appointments that is to be scheduled for the patient;

receive a request from the remote computer to schedule the patient for an appointment that has been selected from the list of available appointments;

update the database to indicate that the patient is scheduled for the selected appointment and that the selected appointment is no longer available;

transmit an appointment confirmation message for display by said remote computer;

receive a request from a remote computer to view a master schedule of all scheduled pre-admission tests for a given testing facility;

compile the master schedule of all scheduled pre-admission tests for a given testing facility;

transmit the master schedule of scheduled pre-admission tests for display by the requesting remote computer;

generate an order for at least one lab test that is to be performed on the patient during pre-admission testing and transmit the order to the facility where the lab test is going to be performed;

receive a report that was generated during the ordered lab test from a remote computer;

transmit the report to the database;

receive a request from a remote computer to view said report; and transmit the report to the remote computer for viewing.

21. A system according to claim 20, wherein said patient information comprises patient demographic and medical information and where said one or more servers is further adapted to:

transmit the patient information to the database prior to the scheduled PAT appointment.

22. A system according to claim 21, wherein said one or more servers is further adapted to:

receive a request from a remote computer to view the patient information; and transmit the patient information to said remote computer for viewing.

23. A system according to claim 21, wherein said one or more servers is further is adapted to receive an access key from a remote computer for use in inputting patient demographic and medical information from a remote location.

24. A system according to claim 20, wherein said one or more servers is further adapted to:

determine whether the scheduled pre-admission test is scheduled for the current day;

transmit a text to the physician that will perform the pre-admission test if the PAT appointment must be done on the current day.

25. A computerized method for pre-admission testing comprising the steps of:

receiving from a remote computer a request to access a web server and to schedule a pre-admission test for a patient;

transmitting to said remote computer a request to provide patient information for the patient requiring a pre-admission test;

receiving from said remote computer the requested patient information;

generating a list of valid available pre-admission test appointments for the patient from pre-admission testing scheduling data electronically retrieved from a database;

transmitting the list of valid available pre-admission test appointments for display by the remote computer;

prompting the remote computer to select an appointment from those provided on the list of available appointments that is to be scheduled for the patient;

receiving a request from the remote computer to schedule the patient for an appointment that has been selected from the list of available appointments;

updating the database to indicate that the patient is scheduled for the selected appointment and that the selected appointment is no longer available;

transmitting an appointment confirmation message for display by said remote computer;

receiving a request from a remote computer to view the master schedule of all scheduled pre-admission tests for a given testing facility;

compiling a master schedule of all scheduled pre-admission tests for a given testing facility;

transmitting the master schedule of scheduled pre-admission tests for display by the requesting remote computer;

receiving a request from a remote computer to view a list of at least one lab test that must be performed on the patient during pre-admission testing to clear the patient for an upcoming medical procedure;

generating a list of at least one lab test that must be performed on the patient during pre-admission testing;

transmitting the generated list of at least one lab test to the remote computer for viewing;

receiving a request to amend the list of at least one lab test by adding at least one lab test to the list; and amending the list of the at least one lab test as requested by the remote computer.

26. The computerized method of claim 25 where said information pertaining to a patient comprises the date on which the patient is scheduled to undergo the medical procedure and the type of medical procedure that is to be performed on the patient.

27. The computerized method of claim 25 further comprising the steps of:

receiving from a remote computer the results of at least one lab test that was performed on the patient during pre-admission testing; and transmitting the results to the database for storage.

28. The computerized method of claim 27 further comprising the steps of:
   searching the database for the lab test results;
   associating the lab test results with a facility where the patient is scheduled to undergo the upcoming medical procedure; and
   sending the results to said facility for viewing.

29. The computerized method of claim 28 wherein said results are sent to said facility via fax.

30. The method of claim 27 further comprising the step of sending a request to the remote computer to indicate whether additional labs are required for pre-admission testing.

31. The method of claim 25 further comprising the steps of:
   determining whether the pre-admission test has been scheduled for the current day; and
   when the pre-admission test has been scheduled for the current day, electronically sending a message from the server to a text messaging system which causes a text message to be sent to an employee of the pre-admission testing facility where the appointment will be taking place to prepare the testing facility for the patient's arrival.

32. The method of claim 25 further comprising the steps of:
   transmitting to a remote computer a request for medical history information for the patient;
   receiving the requested medical history information from the remote computer to which the request for medical history information was sent;
   generating an electronic medical history record for said patient;
   receiving a request to view the electronic medical history record for said patient from a remote computer; and
   transmitting the electronic medical history record to be displayed by the remote computer requesting to view said record.

33. The method of claim 32 further comprising the steps of:
   transmitting the generated electronic medical history record to the database for storage.

34. The method of claim 25 further comprising the steps of:
   receiving a request from a remote computer to alter the master schedule; and
   altering the master schedule as requested by the remote computer.

35. The method of claim 25 further comprising the steps of:
   prompting a remote computer for an access key;
   receiving an access key from the remote computer;
   associating the received access key with the patient that has been scheduled for a pre-admission test;
   prompting the remote computer for information pertaining to the patient that has been scheduled for a pre-admission test;
   receiving the requested information from the remote computer; and
   transmitting the received data to the database for storage.

36. The method of claim 25 further comprising the steps of:
   receiving a request to transmit documents to a specified facility;
   generating instructions for a fax module to fax said documents to said facility; and
   transmitting said instructions to said fax module.

37. The method of claim 36 wherein said facility is where the patient is scheduled to undergo the upcoming medical procedure and said documents comprise a form required by said facility prior to the medical procedure being completed.

38. The method of claim 37 where said documents comprise a report generated during the scheduled pre-admission test.

39. The method of claim 25 further comprising the steps of:
   transmitting a request to a remote computer to enter pre-admission test results that were generated during the patient's scheduled pre-admission test;
   receiving the pre-admission test results; and
   transmitting the pre-admission test results to the database.

40. The method of claim 39 where said pre-admission test results comprise electronic EKG reports.

41. The method of claim 39 further comprising the step of associating the received pre-admission test results with the patient on whom the test was run prior to storing said test results is the database.

42. The method of claim 39 further comprising the steps of:
   comparing the received pre-admission test results with the list of at least one test that must be performed on the patient during pre-admission testing; and
   determining whether the patient is cleared for the scheduled medical procedure.

43. The method of claim 42 further comprising the step of sending notice to the facility that will be performing the scheduled medical procedure that the patient has been cleared for said procedure.

44. The method of claim 25 where said master schedule of all scheduled pre-admission tests for a given testing facility is compiled daily.

45. The method of claim 25 where said master schedule of all scheduled pre-admission tests for a given testing facility comprises a telephone number of a patient scheduled for a pre-admission test.

46. The method of claim 25 further comprising the step of:
   receiving notification from a remote computer that the upcoming medical procedure should be canceled because the patient did not pass the pre-admission test.

47. The method of claim 25 further comprising the step of:
   receiving notification from a remote computer that the upcoming medical procedure should be rescheduled because the patient did not pass the pre-admission test.

* * * * *